(12) United States Patent
Floeter

(10) Patent No.: US 7,524,524 B2
(45) Date of Patent: Apr. 28, 2009

(54) TRIGLYCERIDE FAT

(75) Inventor: Eckhard Floeter, Vlaardingen (NL)

(73) Assignee: Unilever Bestfoods, North America, division of Conopco, Inc., Englewood Cliffs, NJ (US)

( * ) Notice: Subject to any disclaimer, the term of this patent is extended or adjusted under 35 U.S.C. 154(b) by 788 days.

(21) Appl. No.: 10/510,380

(22) PCT Filed: Mar. 10, 2003

(86) PCT No.: PCT/EP03/02625

§ 371 (c)(1),
(2), (4) Date: Oct. 5, 2004

(87) PCT Pub. No.: WO03/084337

PCT Pub. Date: Oct. 16, 2003

(65) Prior Publication Data

US 2005/0220965 A1    Oct. 6, 2005

(30) Foreign Application Priority Data

Apr. 9, 2002    (EP) ................... 02076376

(51) Int. Cl.
*A23D 7/00*    (2006.01)
(52) U.S. Cl. .................. 426/607; 426/601; 426/606
(58) Field of Classification Search ............. 426/601, 426/607
See application file for complete search history.

(56) References Cited

U.S. PATENT DOCUMENTS

| | | | |
|---|---|---|---|
| 4,702,928 A | * | 10/1987 | Wieske et al. ............. 426/607 |
| 5,470,598 A | * | 11/1995 | Scavone .................... 426/607 |
| 6,238,926 B1 | | 5/2001 | Liu et al. |

FOREIGN PATENT DOCUMENTS

| | | |
|---|---|---|
| EP | 0 089 082 | 7/1985 |
| EP | 0 470 658 A | 2/1994 |
| EP | 0 530 864 A | 4/1995 |
| GB | 1 107 206 A | 3/1968 |
| GB | 2 350 618 A | 12/2000 |

OTHER PUBLICATIONS

Deffense, E. 1985. JAOCS 62(2)376-385.*
Cornelius, J. A. 1977. Palm Oil and Palm Kernel Oll. Prog. Chem. Fats other Lipids, vol. 15, Pergamon Press, Great Britain, p. 5-27.*
European Search Report on Application No. EP 02 07 6376 dated Sep. 12, 2002.
Chu et al., "*Physical and chemical properties of a lipase-transesterified palm stearin/palm kernel olein blend and its isopropanol-solid and high melting triacylglycerol fractions*", Food Chemistry, vol. 76, No. 3, 2002, pp. 155-164.

* cited by examiner

*Primary Examiner*—Carolyn A Paden
(74) *Attorney, Agent, or Firm*—Gerard J. McGowan, Jr.

(57) ABSTRACT

A fat suited as fat phase for the manufacture of low fat spreads which are stable at elevated ambient temperatures which fat comprises a mixture of triglycerides, in which—2.5 to 5.5 wt. % of the triglycerides are HHH triglycerides,—25 to 65 wt. %, preferably 25 to 55 wt. % of the HHH triglycerides are monoacid triglycerides and the remaining HHH triglycerides are composed of mixed fatty acid residues,—1.5 to 5 wt. % of the triglycerides are HHM and HMH triglycerides,—at least 85 wt. % of the fatty acid residues H in HHM and HMH are palmitic acid residues, where H denotes saturated fatty acid residues having chain lengths larger than 15 carbon atoms and M denotes saturated fatty acid residues having chain lengths of either 12 or 14 carbon atoms and where the M-residue is placed either in the middle or in one of the terminal positions. Such fat phase can be obtained by incorporating in a triglyceride oil a fat A and a fat B where the fat A and the fat B together amount to 6-15 wt. % of the fat and the A/B weigh ratio is in the range 1/9 to 4/6, characterized in that of fat A—at least 50 wt. % of the triglycerides are fully saturated—at least 80 wt. % of the constituting saturated fatty acid residues have a chain length of 16 carbon atoms (P) or 18 carbon atoms (S), the ratio P:S being in the range 75:25-25:75,—up to 5 wt. % of the saturated fatty acid residues have a chain length of 12 or 14 carbon atoms and in that of fat B—at least 20 wt. %, preferably at least 25 wt. % of the triglycerides consist of HHM and HMH triglycerides.

9 Claims, No Drawings

TRIGLYCERIDE FAT

BACKGROUND OF THE INVENTION

1. Field the Invention

The present invention deals with a solid triglyceride fat which is suited to be used as a hardstock fat for the preparation of emulsion spreads and with a process for the preparation of such fat.

2. Description of Related Art

Margarine is an edible emulsion spread consisting of a continuous fat phase and an aqueous phase which is dispersed as fine droplets in the fat phase. The fat phase of margarine and of similar fat continuous emulsion spreads is a mixture of a fat which is fully liquid (the oil part of the fat phase) and a fat which is solid at ambient temperature. For imparting to common margarine a semi-solid, plastic, spreadable consistency this stabilizing and structuring hardstock functionality plays an important role. The crystals of the solid fat denoted as hardstock fat, form a network throughout the liquid oil resulting into a structured fat phase. It also helps to stabilize the emulsion. Because the aqueous phase droplets are fixed within the spaces of the lattice of solid fat crystals, coalescence of the droplets and separation of the heavier aqueous phase from the fat phase is prevented.

The technology of spread processing is well established. The type of fat and the ratio of liquid oil and solid fat are chosen such that after proper processing of the fat blend with an aqueous phase a plastic product with a suitable consistency and mouthfeel is obtained.

Unprocessed liquid vegetable oils are the major ingredient in the composition of margarine fats. Vegetable fats are preferred over animal fats because their high content of unsaturated fatty acid residues enhances the spread's nutritional value. Besides that, vegetable fats are an abundant and relatively cheap resource.

According to the state of the art, the proper functionality of hardstock fats is obtained by subjecting a vegetable fat to a more or less complex process comprising treatments such as blending, fractionation, hydrogenation and interesterification.

Admixing a hardstock fat to a liquid oil aims at obtaining such fat phase that after emulsifying with an aqueous phase and proper cooling and working, a semi-solid, plastic W/O-emulsion results which is easily spreadable, stable at ambient temperatures and which when swallowed gives a pleasant sensory sensation (mouthfeel). The mouthfeel is the overall perception of quick fat melting and the taste of the aqeouos phase which is released during mastication.

It is known that the presence of HMH and HHM triglycerides contributes to a good mouthfeel. H and M denote the fatty acid residues attached to the glyceride backbone, where H means a saturated fatty acid residue having a chain length larger than 15 carbon atoms and M means a saturated fatty acid residue having a chain length of either 12 or 14 carbon atoms placed either in the middle or one of the terminal positions.

Generally, hardstock fats fail to conserve a proper spread consistency when ambient temperatures rise above average. Relying on a higher melting hardstock fat is at variance with the desire of a good oral melt. A waxy mouthfeel is the consequence which is ascribed to the presence of the high melting HHH triglycerides.

The present invention addresses the desire to combine a good oral melt with good consistency even at high ambient temperatures. Particularly at low fat levels such combination could not have been realised.

A good heat stability is shown by the spreads described in EP 0470658. The fat phase contains 6 wt. % of a single fat, fully hydrogenated palm oil or fish oil as hardstock fat. Nearly 6 wt. % of the fat phase necessarily consists of HHH triglycerides. Consequently the resulting spreads show good heat stability but a waxy mouthfeel.

To the contrary a good mouthfeel is reported for the spreads obtained with the fat phase as described in e.g. EP 0089082 which discloses fats with a high content of HMH and HHM triglycerides. Spreads containing such fats are known to be not stable at high ambient temperatures.

The stability problem becomes particularly serious when the fat content of a W/O-spread drops below 55 wt. % and particularly below 40 wt. %. Ordinary hardstock fats increasingly fail to provide heat stability without sacrificing acceptable mouthfeel.

The challenge to comply with the requirements of both good heat stability and quick mouth melting has triggered investigations which have resulted in the present invention.

SUMMARY OF THE INVENTION

We have found a fat which fat possesses unique properties for use as fat phase in the manufacture of low fat spreads. The fat comprising a mixture of triglycerides, characterised in that
  2.5 to 5.5 wt. % of the triglycerides are HHH triglycerides,
  25 to 65 wt. %, preferably 25 to 55 wt. % of the HHH triglycerides are monoacid triglycerides and the remaining HHH triglycerides are composed of mixed fatty acid residues,
  1.5 to 5 wt. % of the triglycerides are HHM and HMH triglycerides,
  at least 85 wt. % of the fatty add residues H in HHM and HMH are palmitic acid residues,
  where H denotes saturated fatty acid residues having chain lengths larger than 15 carbon atoms and M denotes saturated fatty acid residues having chain lengths of either 12 or 14 carbon atoms and where the M-residue is placed either in the middle or in one of the terminal positions.

The fat can be easily prepared by merely admixing to a triglyceride oil two fats A and B each with a specific triglyceride composition in a ratio chosen from a specific range as follows: incorporating in a triglyceride oil a fat A and a fat B where the fat A and the fat B together amount to 6-15 wt. % of the fat and the A/B weight ratio is in the range 1/9 to 4/6,
  characterized in that of fat A
    at least 50 wt. % of the triglycerides are fully saturated
    at least 80 wt. % of the constituting saturated fatty add residues have a chain length of 16 carbon atoms (P) or 18 carbon atoms (S), the ratio P:S being in the range 75:25-25:75,
    up to 5 wt. % of the saturated fatty acid residues have a chain length of 12 or 14 carbon atoms
  and in that of fat B
    at least 20 wt.%, preferably at least 25 wt. % of the triglycerides consist of HHM and HMH triglycerides where H denotes saturated fatty acid residues having chain lengths larger than 15 carbon atoms and M denotes saturated fatty acid residues having chain lengths of either 12 or 14 carbon atoms and where the M-residue is placed either in the middle or in one of the terminal positions.

DETAILED DESCRIPTION OF THE INVENTION

The present fat is characterized by the presence of two types of triglycerides denoted as HHH and H2M (HHM and HMH) which fat shows the found beneficial properties provided the following conditions are fulfilled;

The fat comprises a mixture of triglycerides, characterised in that 2.5 to 5.5 wt. % of the triglycerides are HHH triglycerides, 25 to 65 wt. %, preferably 25 to 55 wt. % of the HHH triglycerides are monoacid triglycerides and the remaining HHH triglycerides are composed of mixed fatty acid residues, 1.5 to 5 wt. % of the triglycerides are HHM and HMH triglycerides, at least 85 wt. % of the fatty acid residues H in HHM and HMH are palmitic add residues, where H denotes saturated fatty acid residues having chain lengths lamer than 15 carbon atoms and M denotes saturated fatty acid residues having chain lengths of either 12 or 14 carbon atoms and where the N-residue is placed either in the middle or in one of the terminal positions.

Such fats preferably are prepared by the following process: incorporating in a triglyceride oil a fat A and a fat B where the fat A and the fat B together amount to 6-15 wt. % of the fat and the A/B weight ratio is in the range 1/9 to 4/6, characterized in that of fat A at least 50 wt. % of the triglycerides are fully saturated at least 80 wt. % of the constituting saturated fatty acid residues have a chain length of 16 carbon atoms (P) or 18 carbon atoms (S), the ratio P:S being in the range 75:25-25:75, up to 5 wt. % of the saturated fatty acid residues have a chain length of 12 or 14 carbon atoms and in that of fat B at least 20 wt. %, preferably at least 25 wt. % of the triglycerides consist of HHM and HMH triglycerides where H denotes saturated fatty acid residues having chain lengths larger than 15 carbon atoms and M denotes saturated fatty acid residues having chain lengths of either 12 or 14 carbon atoms and where the M-residue is placed either in the middle or in one of the terminal positions. The process merely consists of blending a triglyceride oil with a fat A and a fat B such that the A/B weight ratio is in the range 1/9 to 4/6.

Fat A must consist for at least 50 wt. % of fully saturated triglycerides and moreover the fatty acid residues constituting those triglycerides must for at least 80 wt. % consist of palmitic acid and stearic acid residues, while the content of lauric acid and myristic acid residues should not exceed 5 wt. %.

Fat B must consist for at least 20 wt. %, preferably at least 25 wt. % of H2M triglycerides.

Fats A and B are not necessarily novel. They may be chosen from prior art fats which comply with the claimed composition.

Presently, for processing of edible fats hydrogenation preferably is avoided. The naturalness trend dictates any interesterification step to be carried out preferably enzymatically, while fractionation preferably is dry fractionation without use of solvents.

Fat A suitably is fully hydrogenated palm oil. Preferably fat A is prepared without use or hydrogenation. A more natural process relies on interesterification and fractionation. A fat is selected which has a high content of stearic acid (>20 wt. %) and a fat with a high content of palmitic add (>20 wt. %). Fats with a high content of stearic acid (S) comprise shea fat, Allanblackia fat and the developed high stearic variants of soybean oil, rapeseed oil and sunflower oil. Fats with a high content of palmitic acid (P) comprise palm oil and cottonseed oil. A high stearic fat and a high palmitic fat are blended in such ratio that the blend complies with the P/S ratio being in the range 75:25-25:75. The blend is subjected to interesterification and then to fractionation. The skilled man knows to choose fractionation conditions so that the collected stearin complies with the following:

at least 50 wt. % of the triglycerides are fully saturated at least 80 wt. % of the constituting saturated fatty acid residues have a chain length of 16 carbon atoms (P) or 18 carbon atoms (S), the ratio P:S being in the range 75:25-25:75, up to 5 wt. % of the saturated fatty add residues have a chain length of 12 or 14 carbon atoms.

Alternatively, the high S fat and/or the high P fat to be used for the preparation of fat A are first fractionated to increase the respective contents of S and P further. The high S fat and the high P fat are blended and interesterified and, optionally, thereafter fractionated so that the composition of the collected stearic fraction complies with the following;

at least 50 wt. % of the triglycerides are fully saturated at least 80 wt. % of the constituting saturated fatty acid residues have a chain length of 16 carbon atoms (P) or 18 carbon atoms (S), the ratio P:S being in the range 75:25-25:75, up to 5 wt. % of the saturated fatty acid residues have a chain length of 12 or 14 carbon atoms.

Either route delivers a fat possessing a hardstock functionality which is similar to that of fully hydrogenated palm oil.

Examples of suitable non-hydrogenated fats B are found among the well known interesterified mixtures of palm oil with either palm kernel oil or coconut oil. Optionally fractions of those oils can be used. Preferably the interesterified mixture of palm oil stearin and palm kernel oil (62/38) is used.

Particularly at ambient temperatures exceeding 25° C. the combined presence of fats A and B in a fat phase shows—in contrast to traditional hardstock fats—an ability to ensure heat stability of a spread containing said fat phase. That ability becomes even more pronounced when the fat content of the spread drops below 50 wt. % or even below 40 wt. %. This functionality is obtained with a relatively low contribution of saturated fatty acids by the hardstock fat not exceeding 14 wt. % on total fat blend. So the total saturated fatty acids content of the spread's fat phase can be kept below 25 wt. % and in special cases even below 20 wt. %.

Without wishing to be bound by theory we believe that the beneficial combination of heat stability and good oral perception is based on the special structure of fine crystals which crystal structure is induced by the combined presence of specific HHH triglycerides and specific H2M triglycerides. While the HHH triglycerides should have a composition of highly mixed fatty acids, the H2M triglycerides contain H-residues which are much less mixed. The fatty acid residues (H) of the H2M triglycerides consist predominantly—more than 65 wt %, prefentially more than 75 wt %—of palmitic acid.

These two groups of specific triglycerides, HHH and H2M, essentially have to be obtained by blending separate fats A and B, each of which is needed for its contribution to the unique H-residues composition of the final fat.

The described fat phase can be used for the manufacture of fat continuous emulsion spreads which form part of the invention.

A spread manufacturing process comprises the steps emulsifying 50-80 wt. % of an aqueous phase with 20-50 wt. % of a fat phase and cooling and working the emulsion to obtain a spreadable emulsion, characterized in That a fat phase is used according to the present invention as follows: a fat comprising a mixture of triglycerides, characterised in that 2.5 to 5.5 wt. % of the triglycerides are HHH triglycerides, 25 to 65 wt. %, preferably 25 to 55 wt. % of the HHH triglycerides are monoacid triglycerides and the remaining HHH triglycerides are composed of mixed fatty add 1.5 to 5 wt. % of the triglycerides are HHM and HMH triglycerides, at least 85 wt. % of the fatty add residues H in HHM and HMH are palmitic acid residues, where H denotes saturated fatty acid residues having chain lengths larger than 15 carbon atoms and M denotes saturated fatty add residues having chain lengths of either 12 or 14 carbon atoms and where the M-residue is placed either in the middle or in one of the terminal positions.

The liquid oil part of the fat phase can be any commodity oil generally used for spread manufacture such as rapeseed oil, sunflower oil, soybean oil and mixtures of such oils.

The fat phase contains 6-15 wt. % of the added amounts of fats A and B. For nutritional reasons (low saturated fatty acids content) and for cost reasons preferably the lower amounts of the range are chosen.

Although the spreads of the invention are said to be prepared with a vegetable fat phase, the invention also comprises spreads where a part of the fat phase has been substituted by dairy fat.

The aqueous phase may have any composition which is common for spread manufacture and which comprises the usual spread ingredients such as water, one or more emulsifiers, gelling and/or thickening agents, salt, colouring agent, flavour, a preservation agent and dairy proteins.

The aqueous phase may also contain a dispersed fat phase so that eventually an O/W/O-emulsion would result which is a subspecies of the spreads according to the present invention.

For the preparation of the spread use is made of common spread manufacturing technology:

Suitably the aqueous phase and the fat phase are prepared by mixing the respective ingredients. Then both phases are emulsified. The crude pre-emulsion is subjected to the usual cooling and working treatments employing scraped surface heat exchangers and pin stirrers so that eventually a plastic spread product is obtained.

Such process employs established technology well known to the man skilled in the art. Details can be found in various textbooks such as K. A. Alexandersen, Margarine Processing Plants and Equipment (Vol. 4, Bailey's Industrial Oil and Fat Products, Wiley and Sons Inc., New York 1996).

Preferably the invented spread is prepared with only natural ingredients.

Preferably the content of saturated fatty acids in the spread of the invention is less than 25 wt. %, preferably less than 20 wt. % on total fat phase.

The following examples illustrate the invention.

EXAMPLE 1

Three 40% fat W/O-spreads A, B and C have been prepared starting from a pre-mix of which the fat phases had the composition according to Table I.

B and C have been prepared for comparison and are outside the claim. Ingredients of the pre-mix of spreads A, B and C:

| Pre-mix | wt. % |
| --- | --- |
| Fat phase | 40 |
| Bolec ZT | 0.32 |
| Hymono 8903 | 0.3 |
| Flavour | trace |
| B-carotene | 0.048 |
| Water | 58.6 |
| K-sorbate | 0.073 |
| Whey protein | 0.55 |
| Salt | 0.1 |
| Citric acid | 0.05 |
| End pH | 4.6 |

TABLE I

| | Spread | | |
| --- | --- | --- | --- |
| | A | B (comparison) | C (comparison) |
| Fat phase components (wt. %) | | | |
| Liquid oil | 89% rapeseed oil | 89% rapeseed oil | 87% rapeseed oil |
| Structuring fat | 2% PO58 (2) 9% fat B (1) | 11% in (fhPK/fhPO) (3) | 4% POs (4) 9% fat B (1) |
| Fat phase composition (wt. %) | | | |
| Saturated fatty acids | 15.8 | 17.0 | 16.4 |
| Total HHH | 3.66 | 2.0 | 3.3 |
| PPP | 1.72 | 0.17 | 2.66 |
| SSS | 0.27 | 0.36 | Traces |
| Monoacid TG | 54% of HHH | 27% of HHH | 80% of HHH* |
| PSP | 0.72 | 0.21 | 0.19 |
| PPS | 0.34 | 0.43 | 0.45 |
| PSS | 0.58 | 0.55 | Traces |
| SPS | 0.04 | 0.28 | Traces |
| H2M | | | |
| HHM | 1.67 | 2.53 | 1.6 |
| HMH | 0.83 | 1.27 | 0.8 |
| H in H2M | | | |
| P | 93.4 | 40.8* | 93.4 |
| S | 6.3 | 58.9 | 6.3 |
| A | 0.3 | 0.3 | 0.3 |

*Outside claim specification
(1) Fat B is a chemically interesterified blend of 38 wt. parts of palm kernel fat and 62 wt. parts of dry fractionated palm oil stearin (slip m.p. 56° C.).
(2) PO58: fully hydrogenated palm oil (slip m.p. 58° C.)
(3) A common chemically interesterified blend of 57 wt. parts of fully hydrogenated palm kernel fat and 43 wt. parts of fully hydrogenated palm oil (slip m.p. 58° C.).
(4) Dry fractionated palm oil stearin (slip m.p. 56° C.).

The ingredients mixture was stored at 60° C. prior to processing. After addition of the monoglyceride, salt and flavour, the premix was processed at a throughput of 80 kg/hour through a traditional A-A-A-C sequence of scraped surface heat exchangers (A-units) and a crystallizer (pin stirrer or C-unit). The speed of the A-units was set to 900 rpm, the speed of the C-unit (1.5 l volume) was 1200 rpm. The exit temperature of the last A-unit was approximately 7° C. and the exit temperature of the C-unit was approximately 13° C. The processed spread was filled into 250 g plastic tubs and stored at 15° C. for one week.

For each of the spreads A, B and C a part of the tubs was exposed to 20° C. and another part to 25° C. After one day storage at 25° C. an expert panel (n=6) assessed the spreads A, B and C, prepared with fat phases A, B and C respectively, on heat stability. After subsequent storage for one day at 10° C. these were assessed further on spreadability and mouthfeel.

When judging mouthfeel a combination of melting sensation, flavour perception and salt release was rated. The assessment also included the persistance of a waxy mouthfeel that remains after swallowing the spread.

For spreadability rating it is assessed how smoothly the margarine is spread on a standard surface (waxed paper) and whether the resulting layer has an appealing appearance. Table II shows the assessment ratings on a 1-5 scale (5 being the best).

TABLE II

Quality assessment

|  | Spread | | |
| --- | --- | --- | --- |
|  | A | B (comparison) | C (comparison) |
| Mouthfeel | 4 | 4.5 | 3 |
| Spreadability | 4.5 | 3.5 | 2.5 |
| Heat stability | No phase separation | Slight oil separation at 25° C. | Serious oil separation at 25° C. |

The stability of the spreads against structure desintegration as a consequence of temperature stress was evaluated through exposure of the sample to 20° C. and 25° C. for 24 hours. See Table II.

Spread A withstood the high ambient temperature without any sign of loosing water or layering of oil. Spread B showed an thin layer of oil at 25° C. Comparison spread C, however, showed an unacceptable layer of oil at 25° C.

The assessment of the three spreads clearly showed that a 40% fat spread prepared according to the invention when assessed on temperature stability, oral perception and (low) saturated fat content scored better in comparison with the prior art spreads.

EXAMPLE 2

Two spreads D and E were prepared with the composition and according to the procedure of example 1 with the differences that the aqueous phase of the product was stabilized by 1 wt. % (on spread) of gelatine and only 38 wt. % of fat phase was used.

The spreads contained the fat phases D and E resp. as specified in Table III. Spread E, being outside the claim, was prepared for comparison.

Both spreads D and E were found to be stable against phase separation when exposed to the elevated temperatures as described in example 1. However, in terms of mouthfeel, spread D significantly outperformed spread E. The latter spread not only suffered from a waxy mouthfeel after consumption, it lacked any oral melting sensation. Also the flavour release was not acceptable in comparison with spread

TABLE III

|  | Spread | |
| --- | --- | --- |
|  | D | E (comparison) |
| Liquid oil | 87% Rapeseed oil | 92% Rapeseed oil 8% PO58 (1) |
| Structuring fat | 4% stearin fat (2) 9% fat B (3) | |

TABLE III-continued

|  | Spread | |
| --- | --- | --- |
|  | D | E (comparison) |
| Fat phase composition in wt. % | | |
| Saturated fatty acids | 16.6 | 14.3 |
| Total HHH | 3.9 | 7.64 |
| PPP | 1.7 | 0.58 |
| SSS | 0.21 | 1.09 |
| Monoacid TG | 49% | 22%* |
| PSP | 0.45 | 2.88 |
| PPS | 0.74 | 0.58 |
| PSS | 0.54 | 2.34 |
| SPS | 0.25 | 0.15 |
| H2M | | |
| HHM | 1.53 | 0.30* |
| HMH | 0.76 | 0.14* |
| H in H2M | | |
| P | 93.4 | 44.9 |
| S | 6.3 | 55.0 |
| A | 0.3 | 0.1 |
| Spread quality assessment | | |
| Heat stability 25° C. | Good | Good |
| Oral melt | Fine | Absent |
| Waxy mouthfeel | Absent | Persistent |
| Flavour release | Good | Not satisfactory |

*Outside claim specification
(1) PO58: fully hydrogenated palm oil
(2) The stearin fat is prepared by (chemical) interesterification of 50 wt. parts of palm oil with 50 wt. parts of sheanut butter. The product is subsequently fractionated at such temperature that the stearin fraction contains only HHH triglycerides.
(3) Fat B is a chemically interesterified blend of 38 wt. parts of palm kernel fat and 62 wt. parts of dry fractionated palm oil stearin (slip m.p. 56° C.).

The invention claimed is:

1. A process suited for the preparation of a triglyceride fat, comprising a mixture of triglycerides, characterized in that
   2.5 to 5.5 wt. % of the triglycerides are HHH triglycerides, 25 to 65 wt. %, of the HHH triglycerides are monoacid triglycerides and the remaining HHH triglycerides are composed of mixed fatty acid residues,
   1.5 to 5 wt. % of the triglycerides are HHM and HMH triglycerides,
   at least 85 wt. % of the fatty acid residues H in HHM and HMH are palmitic acid residues,
where H denotes saturated fatty acid residues having chain lengths larger than 15 carbon atoms and M denotes saturated fatty acid residues having chain lengths of either 12 or 14 carbon atoms and where the M-residue is placed either in the middle or in one of the terminal positions, comprising incorporating in a triglyceride oil a fat A and a fat B where the fat A and the fat B together amount to 6-15 wt. % of the fat and the A/B weight ratio is in the range 1/9 to 4/6,
characterized in that of fat A
   at least 50 wt. % of the triglycerides are fully saturated
   at least 80 wt. % of the constituting saturated fatty acid residues have a chain length of 16 carbon atoms (P) or 18 carbon atoms (S), the ratio P:S being in the range 75:25 - 25:75,
   up to 5 wt. % of the saturated fatty acid residues have a chain length of 12 or 14 carbon atoms
and in that of fat B
   at least 20 wt. % of the triglycerides consist of HHM and HMH triglycerides.

2. Process according to claim 1, characterized in that fat A is obtained by
   1. Selecting a fat which contains >20 wt. % of stearic acid and a fat which contains >20 wt. % of palmitic acid,
   2. Blending both fats in such ratio that the blend complies with the P/S ratio of claim 1,
   3. Subjecting the blend to interesterification,
   4. Subjecting the interesterified fat to fractionation under such conditions that the composition of the collected stearin complies with the fat A specifications of claim 1.

3. Process according to claim 1, characterized in that fat A is obtained by
   1. Selecting a fat which contains >20 wt. % of stearic acid and a fat which contains >20 wt. % of palmitic acid,
   2. Fractionating the high stearin fat and/or the high palmitic fat,
   3. Blending the high stearin fat and the high palmitic fat at least one of these being a fractionated fat,
   4. Interesterifying the blend, the conditions for blending and for the fractionation of step 2 and step 4 being chosen such that the composition of the stearin collected after step 4 complies with the fat A specifications of claim 1.

4. The process according to claim 3 further comprising fractionating the interesterified blend of step 4.

5. Process according to claim 1, where in fat B the wt. ratio of oleic acid and linoleic acid residues is more than 3.

6. Process according to claim 1, where either fat A or fat B or both are non-hydrogenated fats.

7. Process according to claim 1, where either fat A or fat B or both are enzymatically interesterified fats.

8. Process according to claim 1, where either fat A or fat B or both have been obtained without the use of wet fractionation.

9. The process according to claim 1 wherein at least 25 wt. % of the triglycerides of Fat B consist of HHM and HMH triglycerides.

* * * * *